(12) United States Patent
Bryans et al.

(10) Patent No.: US 6,846,953 B1
(45) Date of Patent: Jan. 25, 2005

(54) AROMATIC AMIDES

(75) Inventors: Justin Stephen Bryans, Cambridge (GB); John Colm O'Toole, Cambridge (GB); David Christopher Horwell, Cambridge (GB)

(73) Assignee: Warner Lambert Company, Morris Plains, NJ (US)

( * ) Notice: Subject to any disclaimer, the term of this patent is extended or adjusted under 35 U.S.C. 154(b) by 0 days.

(21) Appl. No.: 10/019,993

(22) PCT Filed: May 10, 2000

(86) PCT No.: PCT/GB00/01788

§ 371 (c)(1),
(2), (4) Date: May 6, 2002

(87) PCT Pub. No.: WO00/68184

PCT Pub. Date: Nov. 16, 2000

Related U.S. Application Data
(60) Provisional application No. 60/133,359, filed on May 10, 1999.

(30) Foreign Application Priority Data

Jun. 26, 1999 (DE) .......................................... 199 29 331

(51) Int. Cl.[7] .............................................. C07C 313/02
(52) U.S. Cl. ...................................... 562/620; 562/624
(58) Field of Search .............................. 562/173, 184, 562/620, 624

(56) References Cited

U.S. PATENT DOCUMENTS

| | | | | |
|---|---|---|---|---|
| 3,016,382 A | | 1/1962 | Wright et al. ................ | 260/294 |
| 3,101,339 A | * | 8/1963 | Zeile .......................... | 546/44 |
| 3,163,654 A | | 12/1964 | Hiltmann et al. .......... | 260/294 |
| 3,573,320 A | | 3/1971 | Jansen et al. ............... | 260/305 |
| 4,180,522 A | | 12/1979 | Kane et al. .................. | 260/562 |
| 4,186,208 A | | 1/1980 | Kane et al. .................. | 424/324 |
| 4,203,988 A | | 5/1980 | Bolhofer et al. ........... | 424/266 |
| 4,241,072 A | | 12/1980 | Bolhofer ..................... | 424/270 |
| 4,260,679 A | | 4/1981 | Tsuda et al. ................. | 435/10 |
| 4,286,106 A | | 8/1981 | Kane et al. .................. | 564/220 |
| 4,293,703 A | | 10/1981 | Bolhofer ..................... | 548/337 |
| 4,681,898 A | * | 7/1987 | Nadelson .................... | 514/619 |
| 4,877,876 A | | 10/1989 | Tsuji et al. .................. | 544/133 |
| 4,952,584 A | | 8/1990 | Thompson et al. ......... | 514/292 |
| 5,001,159 A | | 3/1991 | Hoornaert et al. ......... | 514/619 |
| 5,075,325 A | | 12/1991 | Hoornaert et al. ......... | 514/357 |
| 5,372,932 A | | 12/1994 | Friedman et al. ........... | 435/7.9 |
| 5,403,842 A | | 4/1995 | Leonardi et al. ........... | 514/252 |
| 5,453,533 A | | 9/1995 | Luo et al. .................... | 560/142 |
| 5,464,788 A | * | 11/1995 | Bock et al. ............ | 514/253.12 |
| 5,474,994 A | | 12/1995 | Leonardi et al. ........... | 514/218 |
| 5,605,896 A | | 2/1997 | Leonardi et al. ........... | 514/218 |
| 5,654,301 A | | 8/1997 | Kohn et al. ............... | 514/231.2 |

FOREIGN PATENT DOCUMENTS

| | | | |
|---|---|---|---|
| EP | 0 084 292 | * | 7/1983 |
| EP | 0154190 | | 9/1985 |
| FR | 2073286 | | 1/1971 |
| GB | 855770 | | 12/1960 |
| WO | WO 9813336 | | 4/1998 |
| WO | WO 9850343 | | 11/1998 |

OTHER PUBLICATIONS

Sekiya, CA 113:190946, abstract of JP 02138161, 1990.*
Dombro, CA 60:93472, abstract, Biochem. Pharmacol. 13(4), 569–576, 1964.*
Dombro, CA 63:34608, abstract of Nature, 206(4984), 631–632, 1965.*
Diurno, CA 122:230112, abstract of Med Chem Research, 4(9), 578–587, 1994.*
Elslager et al., "Respiratory Drugs. VIII. Ester and Amide Congeners of Amodiaquine, Hydroxychloroquine, Oxychloroquine, Primaquine, Quinacrine and Related Substances as Potential Long–Acting Antimalarial Agents", *J. Med. Chem.*, (1969), vol. 12, No. 4, pp. 600–607.
CA 60: 16390f, *Chemical Abstract*.
Ronsisvalle et al., "Synthesis and pharmacological properties of N–thienyl alkylenediamines", *Eur. J. Med. Chem.* (1988), vol. 23, No., 6, pp. 553–559.
Sugimoto et al., "Studies on the Synthetic Analgesics. XVII. Syntheses of 2–(N–tert–Aminoalkylacylamino)thiophen", *Chem. Pharm. Bull.*, (1962), (Tokyo) vol. 10, No. 11, pp. 1061–1064.
Pifferi et al., "Synthesis and Antihypertensive Properties of New 3–Hydrazinopyridazine Derivatives", *J. Med. Chem.*, (1975), vol. 18, No. 7, pp. 741–746.
CA 60: 2911e, *Chemical Abstract*.
Bolhoffer et al., "Inhibitors of Gastric Acid Secretion: Antisecretory 2–Pyridylurea derivatives", *J. Med. Chem.*, (1983), vol. 26, No. 4, pp. 538–544.
Geiger et al., "Stereochemical Studies on Drugs, Part 11. Conformation of alkylated 2–acylaminopyridines and their relation with morphine structure", *Eur. J. Med. Chem.*, (1982), vol. 17, No. 3, pp. 207–215.
CA 61: 10659 d, e, f, *Chemical Abstracts*.
Wright, et al., "Synthetic Analgesics. II. Basic Anilides and Carbanilates", *J. Org. Chem.*, (1961), vol. 26, pp. 476–485.
Wright, et al., "Synthetic Analgesics. III. Basic Anilides and Carbanilates Containing the Phenalkyl; Moiety", *J. Org. Chem.* (1961), vol. 26(2), pp. 485–490.

(List continued on next page.)

*Primary Examiner*—D. Margaret Seaman
(74) *Attorney, Agent, or Firm*—Suzanne M. Harvey; David R. Kurlandsky; Charles W. Ashbrook

(57) ABSTRACT

Aromatic and heteroaromatic amides of the formula

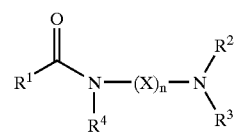

where $R^1$, $R^2$ and $R^3$ can be alkyl, X is alkylene, and $R^4$ is an unsubstituted or substituted aromatic or heteroaromatic group such as naphthyl or fluorenyl,
are CNS agents useful for treating pain, depression, anxiety, seizures, and schizophrenia.

22 Claims, No Drawings

OTHER PUBLICATIONS

CA 64: 322e, *Chemical Abstracts*.
CA 63: 5562f, *Chemical Abstracts*.
CA 59: 12704h, *Chemical Abstracts*.
CA 59: 12705a, *Chemical Abstracts*.
Foussard–Blanpin et al, "Structure–activity relation in local anesthetics. II. Amidines and amides", *Ann. Pharm. Fr.,* (1982), vol. 40, No. 3, pp. 231–240.
Courriere et al, "Structure–activity study in a series of local anesthetic agents. I. Physico–chemical properties and molecular orbital study. Correlation with their pharmacodynamical activity", *Eur. J. Med. Chem.,* (1978), vol. 13, No. 2, pp. 121–126.
Hiltmann et al, "2–(Acylamino) pyridine derivatives with morphine agonistic and morphine antagonistic properties", *Arzneim.–Forsch.,* (1974), vol. 24, No. 4, pp. 584–600.
Eckhardt et al, "Mass spectrometric cleavage of a N–substituent from monoacylated 1,3–diaminopropanes", *Org. Mass Spectrum,* (1978), vol. 13, No. 1, pp. 17–19.
Okumura et al., 4–Oxo–1,2,3,4–tetrahydroquinazolines. II. Synthesis of 1–Alkyl–and 1–[2–(Disubstituted amino)ethyl]– 2–methyl–3–aryl–4–oxo–1,2,3,4–tetrahydroquinazolines, *J. Med. Chem.,* (1968), vol. 11, pp. 788–792.
Foussard–Blanpin et al., "Comparative rvations on the inhibition of histamine release by 2–deoxyglucose. Ang.", *Anesth, Analg, Reanim.,* (1968), vol. 25, No. 1, pp. 35–43.
Sam et al, "New Compounds: Amides Derived from 2–(2–Pyridyl) ethylamines," *J. Pharm. Sci.,* (1967), vol. 56, No. 9, pp. 1202–1205.
CA 62: 14538g, *Chemical Abstracts*.
CA 61: 1780c, *Chemical Abstracts*.
CA 59: 13847f,h, *Chemical Abstracts*.
CA 59: 13848a, *Chemical Abstracts*.
CA 55: 24612e,f, *Chemical Abstracts*.
CA 55: 5504i, *Chemical Abstracts*.
CA 55: 5505a, *Chemical Abstracts*.
CA 53: 22507a, *Chemical Abstracts*.
CA 53: 14034e, *Chemical Abstracts*.
Beilstein Registry No. 3302274.
Beilstein Registry No. 3387876.
Beilstein Registry No. 3403499.
Beilstein Registry No. 3408732.
Beilstein Registry No. 3887209.
Beilstein Registry No. 3888888.
Beilstein Registry No. 3889259.
Beilstein Registry No. 321504.
Beilstein Registry No. 3891877.
Guerrera et al., "Synthesis of 1–alkyl–3–dialkylaminoalkylamine[1]benzothieno[2,3–b]pyrazin–2(1H)–ones and their ability to antagonize KCl–induced contractions", *Eur. J. Med. Chem.,* 1996), vol. 31, pp. 607–613.
Elslager et al, "Synthetic Schistosomicides. VIII. N–Mono–and N,N–Dialkyl–N'–(4–arylazo–1–naphthyl)alkylenediamines and Related Compounds", *J. Med. Chem.,* vol. 9, No. 3, p. 378–91.
Elderfield et al, "Synthesis of Simple 2–Phenyl–8–aminoquinoline Derivatives", *J Amer Chem Soc.,* (1946) pp. 1589–1591.
Beilstein Registry No. 281939.
Beilstein Registry No. 302591.
Beilstein Registry No. 339482.

\* cited by examiner

AROMATIC AMIDES

CROSS REFERENCE TO RELATED APPLICATIONS

This application is a 371 filing of PCT/GB00/01788 filed May 10, 2000, priority based on Provisional Application Ser. No. 60/133,359 filed May 10, 1999.

FIELD OF THE INVENTION

This invention provides aromatic amides which are useful CNS agents, especially for treating depression, pain, anxiety, schizophrenia and seizure disorders.

BACKGROUND OF THE INVENTION

Disorders of the central nervous system have become one of the most common and most debilitating diseases currently afflicting mankind. Specific disorders such as depression and schizophrenia are now known to be common afflictions, and are routinely diagnosed. These diseases result in significant losses of an individual's ability to work and to carry out normal daily activities, and in many cases require long term hospitalization or institutionalization. Only recently have new treatments, such as the selective serotonin re-uptake inhibitors for example, become available and are effective for many people. Unfortunately, such agents are not effective for all cases of depression, and indeed can lead to significant adverse reactions in some patients.

Other CNS disorders, such as chronic pain and seizure disorders, are only marginally treatable, and such treatments often are associated with unacceptably high health risks, for instance long term use of narcotic analgesics to treat chronic pain generally results in addiction to the drug being employed, the results of which can be devastating to the patient.

Accordingly, the need continues for new medicines that will effectively treat CNS disorders without imposing unacceptable liability and risk issues. I have now discovered a series of aromatic amides which can be utilized to treat these CNS disorders, and which have a very good risk-to-benefit ratio. The invention compounds are alkyl amides having an aromatic group attached to the amide nitrogen atom.

Several N-aryl alkylamides are known in the prior art. For example, Ronsisvalle et al. described a series of analgesic N-thienyl acetamides in *Eur. J. Med. Chem.* 3: 553–559, 1998.

U.S. Pat. No. 4,203,988 discloses certain N-pyridyl amide derivatives as inhibitors of gastric secretion, while U.S. Pat. No. 3,163,645 discloses N-pyridyl amides as analgesics. U.S. Pat. No. 5,372,931 discloses N-alkoxyphenyl and N-alkoxynaphtyl amides as useful in certain analytical and diagnostic methods.

Elslager et al., in *J. Med. Chem.* 9: 378–91, 1966, describe certain N-naphthyl amides as useful as intermediates in the synthesis of arylazo substituted naphthyl alkylenediamines. Similarly, Elslarger et al., described certain N-quinolyl amides in *J. Med. Chem.* 12: 600–7, 1966.

The compounds provided by this invention are characterized as novel N-aryl amides having good CNS activities, and are thus useful for treating depression, anxiety, pain, schizophrenia, and seizure disorders such as epilepsy.

SUMMARY OF THE INVENTION

This invention provides N-aryl alkylamides defined by Formula I

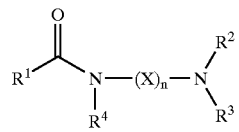

wherein:
$R^1$ is hydrogen, $C_1$–$C_4$ alkyl, or $C_2$–$C_4$ alkenyl;
$R^2$ and $R^3$ independently are hydrogen, $C_1$–$C_4$ alkyl, $C_1$–$C_4$ alkoxy, phenyl or benzyl, or taken together with the nitrogen to which they are attached complete a ring having from 4 to 7 ring atoms, one optionally being oxygen; X is $(CH_2)_n$, $CHMe$-$(CH_2)_{n-1}$ or $(CH_2)_{n-1}$—$CHMe$, n is 1, 2 or 3;
$R^4$ is an aromatic or heteroaromatic group selected from

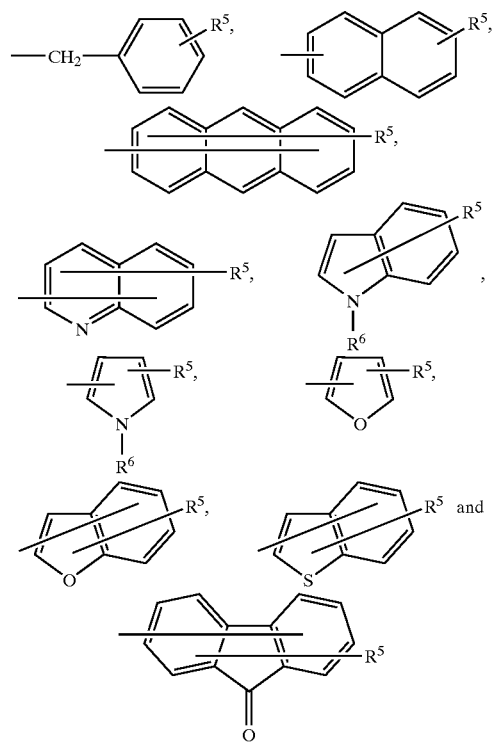

wherein $R^5$ is hydrogen, halogen, $C_1$–$C_4$ alkyl, nitro, $N_3$ or $CF_3$ and $R^6$ is hydrogen, $C_{1-4}$ alkyl, —(C=O)Me, —(C=O)NH_2,

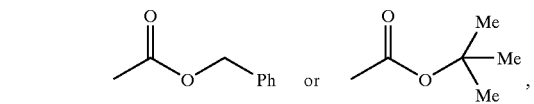

and the pharmaceutically acceptable salts thereof.
Preferred invention compounds have Formula I wherein $R^1$. $R^2$ and $R^3$ independently are $C_1$–$C_4$ alkyl, and R is naphthyl, substituted naphthyl, fluorene or substituted fluorene. Also preferred are the compounds of Formula I wherein n is 2 or 3.

Another embodiment of this invention is a pharmaceutical formulation comprising a compound of Formula I admixed with a pharmaceutically acceptable carrier, diluent or carrier therefor.

The compounds of the instant invention are useful for the treatment of CNS disorders including neurodegenerative disorders, pain, depression, convulsions, anxiety, schizophrenia and seizures.

Neurodegenerative disorders include, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

Pain refers to acute as well as chronic pain.

Acute pain is usually short-lived and is associated with hyperactivity of the sympathetic nervous system. Examples are postoperative pain and allodynia.

Chronic pain is usually defined as pain persisting from 3 to 6 months and includes somatogenic pains and psychogenic pains. Other pain is nociceptive.

Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, IBS and other forms of neuralgia, neuropathic and idiopathic pain syndrome.

A skilled physician will be able to determine the appropriate situation in which subjects are susceptible to or at risk of, for example, stroke as well as suffering from stroke for administration by methods of the present invention.

The compounds of the invention are also useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

The compounds of the instant invention are also expected to be useful in the treatment of anxiety, panic, schizophrenia and seizures as demonstrated by means of standard pharmacological procedures.

The invention also provides a method for treating CNS disorders in mammals, comprising administering a CNS effective amount of a compound of Formula I to a mammal in need of treatment.

DETAILED DESCRIPTION OF THE INVENTION

As used herein, the term "$C_1$–$C_4$ alkyl" means straight and branched carbon chains having from 1 to 4 carbon atoms, for example methyl, ethyl, n-propyl, isopropyl, n-butyl, sec-butyl and tert-butyl.

"$C_2C_4$ alkenyl" means ethylene, 2-propylene and 2- or 3-butylene.

"Halo" means fluoro, chloro, bromo and iodo.

"Substituted aryl" and "substituted heteroaryl" means any of the cyclic ring systems described above having $R^5$ other than hydrogen, for example where $R^5$ is halo, $C_1$–$C_4$ alkyl, nitro or $CF_3$. Typical substituted aryl and substituted heteroaryl groups thus include 3-chloronaphthyl, 4-nitronaphthyl, 4-nitrobenzofuranyl, 3-methylbenzothienyl, and 1-methyl-3-trifluoromethyl indole. These are compounds of Formula I wherein R is a cyclic, bicyclic or tricyclic aromatic or heteroaromatic group bearing a substituent defined as $R^5$, where R is other than hydrogen. The group

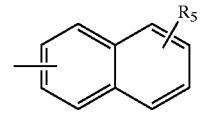

is a naphthyl ring which can be attached to the amide nitrogen (of Formula I) at any ring position. This ring can be substituted at any available ring position by the group $R^5$. Specific examples include:

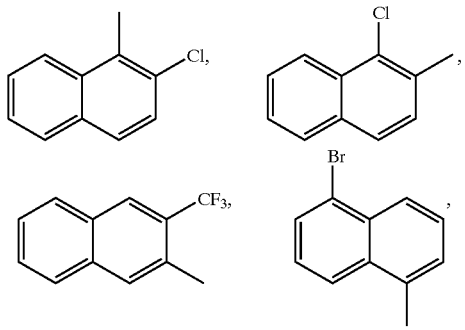

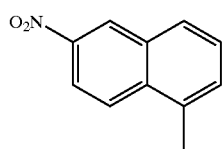 and 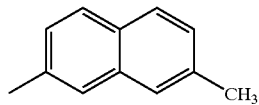
Specific examples of the group:
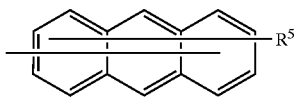
include:
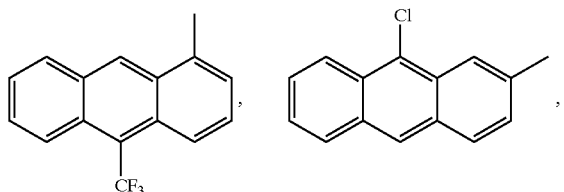
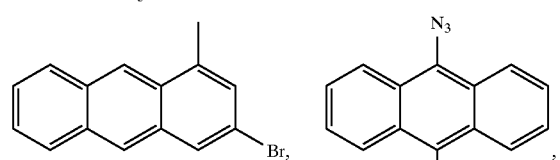
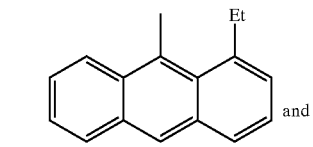
Specific examples of the group:
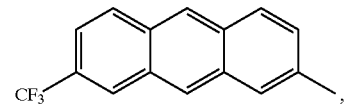
include:
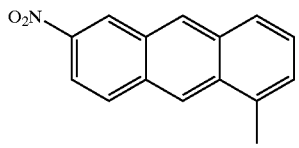
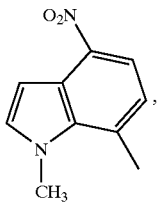, 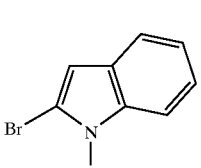 and
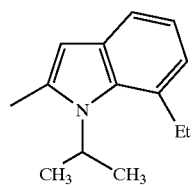
Specific examples of the group:
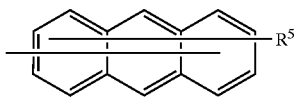
include
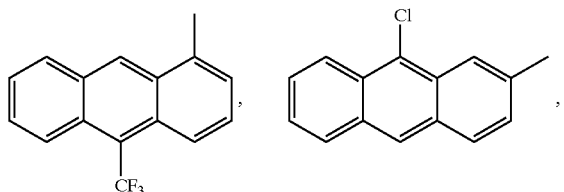 and
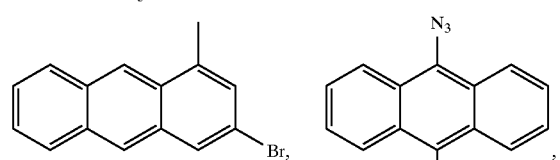
Specific examples of the group: include
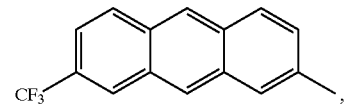
include
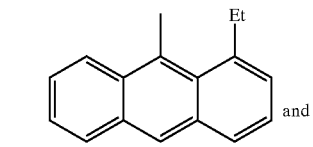 and
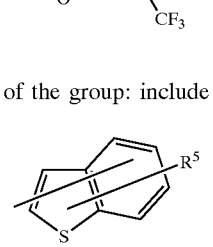
Specific examples of the group:
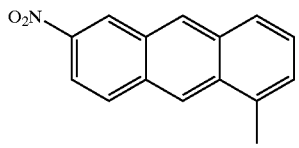

-continued include

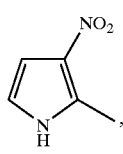 , 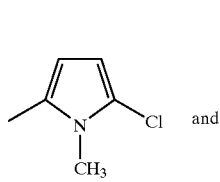 and 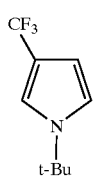

Specific examples of the group:

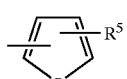

include

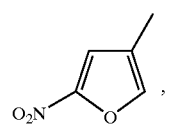 , and 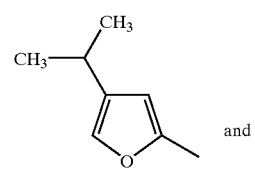

Specific examples of the group:

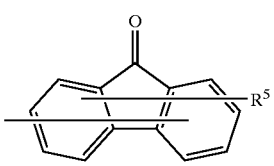

include

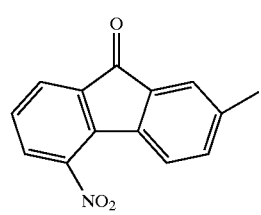 , 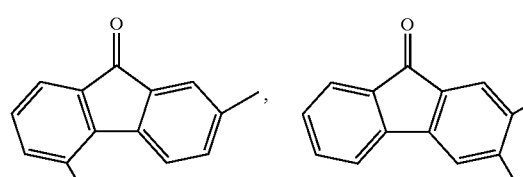 ,

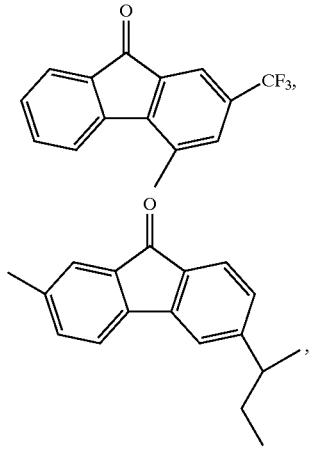 ,

-continued

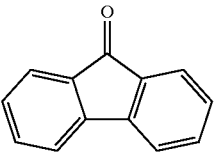 and 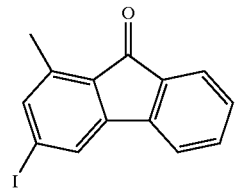

Specific examples of the group:

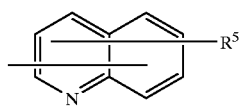

include

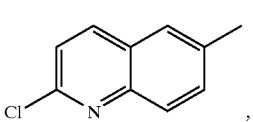 , 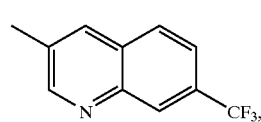 ,

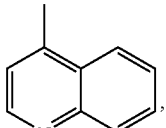 , 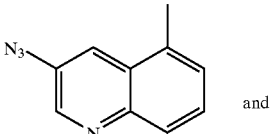 and

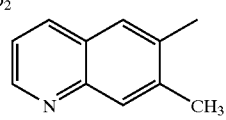

Specific examples of the group:

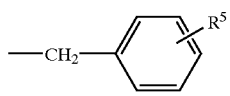

include

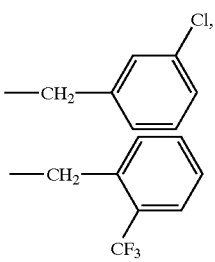 , 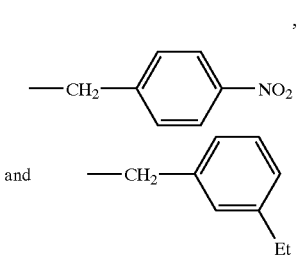 ,

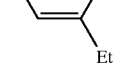 and 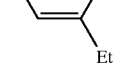

The compounds of this invention are amines and as such they readily form pharmaceutically acceptable salts by reaction with common inorganic and organic acids. Typical acids commonly used to form salts include hydrochloric, nitric, phosphoric, and sulfuric acid, as well as acetic, citric, malonic, tartaric, succinic, salicylic, methanesulfonic, oxalic and benzoic acid. Any common inorganic or organic acid can be utilized to form the pharmaceutically acceptable salts of this invention, and the specific acid to be utilized is well within the skill of the art.

The compounds provided by this invention can be prepared by any of several methods well known to those of ordinary skill in the art of organic chemistry. In a typical synthesis, an N-aryl alkyl diamine is acylated, for example by reaction with an aryl halide, or by coupling an aryl-acid to the amide in the presence of a common peptide coupling reagent such as DCC (dicyclohexylcarbodiimide). Such synthesis can be illustrated by Scheme 1, in which an alkyl diamine is first prepared by reacting a halo substituted acyl halide with an amine $HNR^2R^3$, to give the corresponding halo substituted amide, reacting the halo substituted amide with an aryl amine $ArNH_2$ to give an arylaminoamide, reducing the amide carbonyl to give the corresponding arylamino alkylamine, and then acylating the arylamino nitrogen atom to give a compound of Formula II. The synthetic sequence is illustrated in scheme 1:

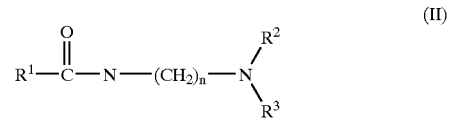

where one or both of $R^2$ and $R^3$ are hydrogen, by reaction with an alkylating agent such as an alkyl halide. The reaction is depicted by scheme 2, which illustrates the synthesis of the primary or secondary amine according to the general scheme shown above, followed by a reaction with a common alkylating agent.

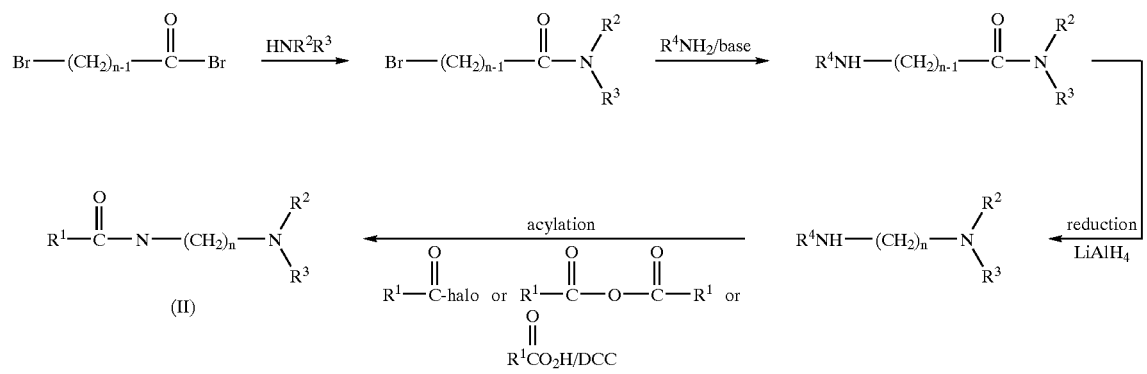

An alternative method for preparing the invention compounds comprises alkylating a terminal primary or secondary amine of the formula Scheme 2

In the above scheme, the halo substituted acid halide is reacted with an amine bearing a group that is easily removed, such as benzyl. This is a normal acylation reaction that is typically carried out in a solvent such as dichloromethane or toluene, and generally is complete within 30 min to 1 h when carried out at a temperature of about 30° C. to about 60° C. The resulting amide is readily isolated by removing the solvent, and is subsequently reacted with an amine $R^4NH_2$ in the presence of a base such as sodium carbonate or triethylamine, and typically in a solvent such as N,N-dimethylformamide or diethyl ether. The resulting amino substituted amide is readily isolated by removing the solvent, and further purification generally is not required. The amino substituted amide is readily reduced by reaction with a reducing agent such as lithium aluminium hydride or sodium borohybride, thus affording an alkylene diamine. The alkylene diamine is coupled to an acyl group, for example by common acylation with an acid anhydride or acid halide (e.g. $R^1$—C(=O)—O—C(=O)—R or $R^1$—C(=O)-halo, or by reacting the free acid $R^1COOH$ with the amine using a coupling reagent such as dicyclohexylcarbodiimide (DCC).

The corresponding amide is next converted to a primary or secondary amine, for instance by removing a group such as benzyl by normal catalytic hydrogenation. The resulting amine is reacted with a common alkylating agent such as an alkyl halide ($R^3$-halo) and the resulting reaction product of Formula I is isolated by removing any reaction solvent and excess alkylating agent. The invention compound can be further purified if desired by routine methods such as crystallization, for example from solvents such as methanol, diethylether, ethyl acetate and the like, or chromatography over solid supports such as silica gel.

Still another way to prepare the invention compounds is to start with an aryl amine ($R^4NH_2$), acylate it with and acyl halide or anhydride to form an amide, and then alkylate the amide with an amino substituted alkyl halide. This process is depicted in Scheme 3 below:

Scheme 3

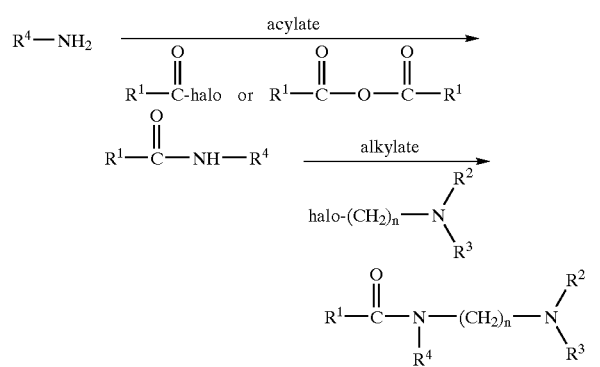

These reactions are carried out under normal organic synthetic conditions. For example, an aryl amine such as 3-naphthylamine can be reacted with acetyl chloride in a solvent such as toluene. A base such as triethylamine can be utilized as an acid scavenger if desired. The reaction is substantially complete within 1 to 2 h when carried out at about 30 to 60° C., and the product amide is readily isolated by removing the reaction solvent. The amine is then alkylated by reaction with an amino substituted amino alkyl halide to produce the invention compound of Formula I.

The synthesis of specific invention compounds is further illustrated by the following detailed example. The examples are representative only, and are not intended to limit the invention in any respect.

EXAMPLE 1

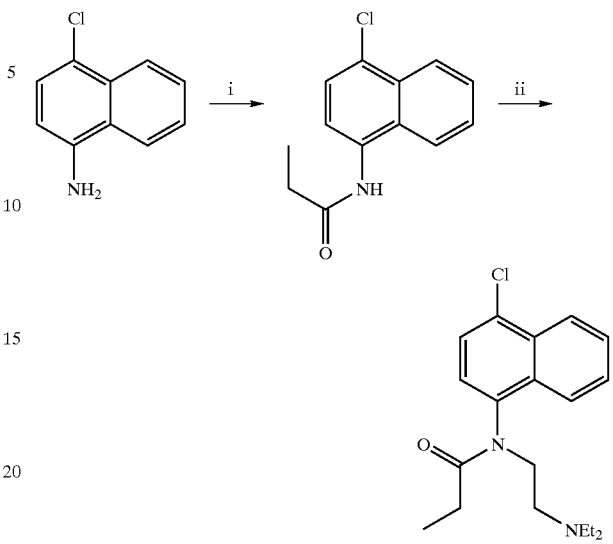

Reagents: (i) propionyl chloride, $Et_3N$ (ii) NaH, $Et_2NCH_2CH_2Cl.HCl$

N-Propionyl 1-amino-4-chloronaphthalene.

To a stirred solution of 1-amino-4-chloronaphthalene (0.70 g, 3.9 mmol) in dichloromethane (50 ml) was added triethylamine (1.0 ml, 7 mmol), followed by propionyl chloride (0.5 ml, 5.8 mmol). After 20 min the mixture was diluted with ethyl acetate (150 ml) and washed with 2N HCl (100 ml) followed by saturated sodium carbonate (100 ml). The organic phase was separated, dried ($MgSO_4$) and the solvent removed in vacuo. The residue was triturated with a mixture of ethyl acetate and heptane, 130 ml, 3:10) to give 0.62 g (67%) of the desired compound as a white solid.

$^1$H NMR 400 MHz ($CDCl_3$): ™ 1.33 (3H, t, J=6 Hz); 2.56 (2H, q, J=6 Hz); 7.47 (1H, br s); 7.52–7.70, 4H, m); 7.84 (1H, m); 8.32 (1H, m).

MS ES$^+$: m/z 236 ([MH$^+$], 16%), 234 ([MH]$^+$, 48%).

IR (thin film) $\lfloor_{max}$ (cm$^-$): 1652, 2922, 3300.

N-Propionyl, N-(2-diethylaminoethyl)-1-amino-4-chloronaphthalene.

To a stirred solution of N-propionyl 1-amino-4-chloronaphthalene (400 mg, 1.7 mmol) in dry dimethylformamide (40 ml) was added sodium hydride (60% dispersion in oil, 0.2 g, 5 mmol). After 20 min, 2-diethylaminoethylchloride hydrochloride (0.4 g, 2.8 mmol) was added and the mixture stirred for a further 2 h. Water (200 ml) was added and the mixture extracted with ethyl acetate (2×100 ml). The organic extracts were combined, dried ($MgSO_4$) and the solvent removed in vacuo. The residue was purified by reverse phase chromatography (methanol:water 7:3) to give 0.27 g (47%) of the desired product as a colorless oil.

$^1$H NMR 400 MHz ($CDCl_3$): ™ 0.97 (9H, m); 1.80 (1H, m); 2.01 (1H, m); 2.50 (4H, m); 2.69 (2H, t, J=7 Hz); 3.34 (1H, m); 4.33 (1H, m); 7.36 (1H, d, J=8 Hz); 7.55–7.70 (3H, m); 7.84 (1H, m); 8.34 (1H, d, J=8 Hz).

MS CI: m/z 233 ([MH]$^+$, 100%).

IR (thin film) $\lfloor_{max}$ (cm$^-$): 1667, 2970.

| Microanalysis for $C_{19}H_{25}N_2OCl$ | | | | | | |
|---|---|---|---|---|---|---|
| Calculated | C | 68.56% | H | 7.57% | N | 8.42% |
| Found | | 68.29% | | 7.78% | | 8.20% |

EXAMPLE 2

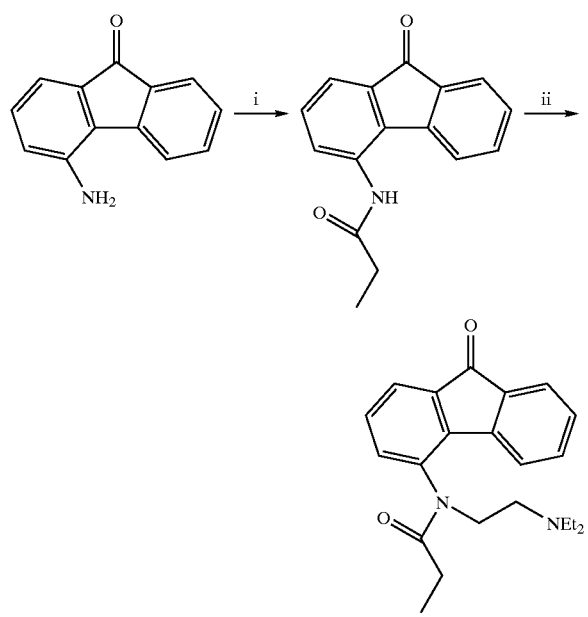

Reagents: (i) propionyl chloride, $Et_3N$; (ii) NaH, $Et_2NCH_2CH_2Cl \cdot HCl$ N-Propionyl 4-amino-9-fluorenone.

To a stirred solution of 4-amino-9-fluorenone (0.20 g, 1.0 mmol) in dichloromethane (40 ml) was added triethylamine (0.5 ml, 3.5 mmol), followed by propionyl chloride (0.5 ml, 5.8 mmol). After 20 min the mixture was diluted with ethyl acetate (150 ml) and washed with 2N HCl (100 ml) followed by saturated sodium carbonate (100 ml). The organic phase was separated, dried ($MgSO_4$) and the solvent removed in vacuao. The residue was purified by flash chromatography (silica, heptane:ethyl acetate 7:3) to give 164 mg (63%) of the desired material as a yellow oil.

$^1$H NMR 400 MHz ($CDCl_3$):™ 1.36 (3H, br t); 2.56 (2H, br q); 7.18–7.38 (4H, m); 7.41–7.60, (2H, m); 7.71 (1H, d, J=8 Hz); 7.83 (1H, br s).

IR (thin film) $v_{max}$ (cm$^-$): 1659, 1716, 3258.

N-Propionyl, N-(2-diethylaminoethyl)₄-amino-9-fluorenone.

N-propionyl 4-amino-9-fluorenone (158 mg, 0.6 mmol) was dissolved in dry dimethylformamide (40 ml) and sodium hydride (60% dispersion in oil, 80 mg, 1.2 mmol). After 20 min, 2-diethylaminoethylchloride hydrochloride (250 mg, 1.4 mmol) was added and the mixture was heated to 80° C. After 10 min the mixture was cooled to room temperature and diluted with water (20 ml). The mixture was diluted with saturated sodium carbonate (150 ml) and the mixture extracted with ethyl acetate (2×70 ml). The organic extracts were combined, dried ($MgSO_4$) and the solvent removed in vacuo. The residue was purified by flash chromatography (silica, dichloromethane:diethyl ether 9:1, and then 1:4) to give 0.16 g (73%) of the desired product as a colorless oil.

$^1$H NMR 400 MHz ($CDCl_3$): ™ 0.95 (6H, t, J=7 Hz); 1.05 (3H, t, J=7 Hz); 2.08 (2H, m); 2.50 (4H, m); 2.69 (2H, m); 3.34 (1H, m); 4.34 (1H, m); 7.30–7.75 (7H, m).

MS CI: m/z 351 ([MH]$^+$, 100%).

IR (thin film) $v_{max}$ (cm$^-$): 1652, 1716, 2970.

| Microanalysis for $C_{22}H_{26}N_2O_2$ | | | | | | |
|---|---|---|---|---|---|---|
| Calculated | C | 75.40% | H | 7.48% | N | 7.99% |
| Found | | 75.55% | | 7.57% | | 7.94% |

EXAMPLES 3–15

By following the general procedure of Examples 1 and 2, several additional compounds of Formula I were prepared and are described in Table I below.

The compounds of Formula I have been evaluated in standard in vivo and in vitro assays routinely used to measure the ability of test compounds to interact with the central nervous system of animals, thereby establishing their utility for treating CNS disorders such as pain, depression, anxiety and schizophrenia. In a typical assay, compounds are evaluated for their ability to bind to the $\alpha_2\delta$ submit of the calcium channel found in animal brain tissue. Significant binding to this receptor indicates a compound's analgesic potential.

In another test, compounds were evaluated for their ability to reduce the hyperalgesia effects of carrageenin in the following assay: nociceptive pressure thresholds were measured in the rat paw pressure test using an analgesimeter (Randall L. O. and Selitto J. J., A method for measurement of analgesic activity on inflamed tissue. Arch. Int. Pharmacodyn 4: 409–419, 1957). Male Sprague-Dawley rats (70–90 g) were trained on this apparatus before the test day. Pressure was gradually applied to the hind paw of each rat Nociceptive thresholds were determined as the pressure (g) required to elicit paw withdrawal. A cutoff point of 250 g was used to prevent any tissue damage to the paw. On the test day, 2 to 3 baseline measurements were taken before animals were administered 100 µl of 2% aqueous carrageenin by intraplantar injection into the right hind paw.

Nociceptive thresholds were taken again 3 h after carrageenin injection to establish that animals were exhibiting hyperalgesia. Animals were orally dosed with a compound of Formula I (by gavage) at 3.5 h after carrageenin injections and nociceptive thresholds were examined at 1 and at 2 h post-carrageenin.

Table 1 presents the biological activity of representative invention compounds when evaluated in the above tests, and in the in vitro $\alpha_2\delta$ binding assay as described by Gee et al. in J. Biol. Chem., 1996; 271: 5776–5879, incorporated herein by reference.

TABLE 1

| Compound | Structure | IC$_{50}$ (μM) at α$_2$δ binding site | Carrageenin induced thermal hyperalgesia in the rat | |
|---|---|---|---|---|
| | | | % MPE* 1 h post dose @ 30 mg/kg p.o. | % MPE* 2 h post dose @ 30 mg/kg p.o. |
| N-Propionyl, N-(2-Diethylaminoethyl)-1-amino-4-chloronaphthalene (Example 1) | 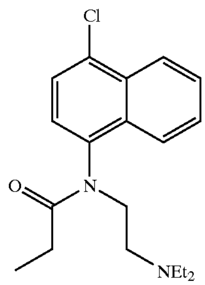 | 0.170 | 51.5 | 22.2 |
| N-Propionyl, N-(2-Diethylaminoethyl)-4-amino-9-fluorenone (Example 2) | 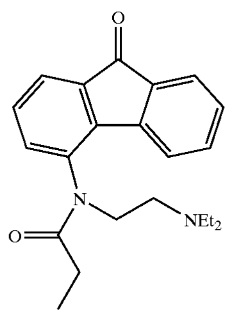 | 0.058 | 1.1 | 6.4 |
| N-Propionyl, N-(2-Diethylaminoethyl)-1-amino-4-bromonaphthalene (Example 3) | 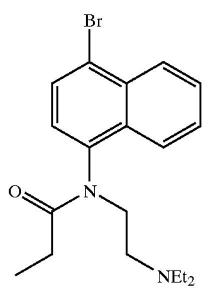 | 0.065 | −2.6 | 7.7 |
| N-Propionyl, N-(N-Morpholino)-1-amino-4-chloronaphthalene (Example 4) | 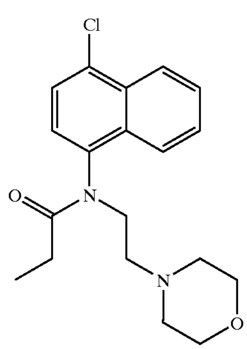 | >10 | 44.8 | 30.7 |

TABLE 1-continued

| Compound | Structure | IC$_{50}$ ($\mu$M) at $\alpha_2\delta$ binding site | Carrageenin induced thermal hyperalgesia in the rat | |
|---|---|---|---|---|
| | | | % MPE* 1 h post dose @ 30 mg/kg p.o. | % MPE* 2 h post dose @ 30 mg/kg p.o. |
| N-Propionyl, N-(2-(3-diethylamino-propyl))-1-amino-4-chloronaphthalene (Example 5) | 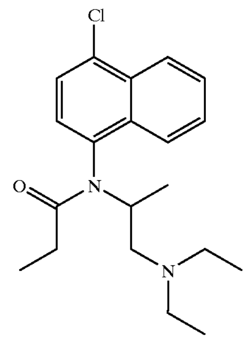 | 5.03 | 23.3 | 27.5 |
| N-Propionyl, N-(2-Diethylaminoethyl)-1-amino-4-azidonaphthalene (Example 6) | 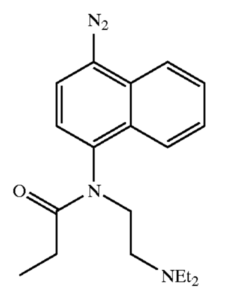 | 0.885 | N/A | N/A |
| N-Propionyl, N-(2-Diethylaminoethyl)-3-chlorobenzylamine (Example 7) | 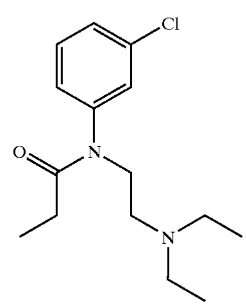 | 1.7 | N/A | N/A |
| N-Propionyl, N-(2-Diethylaminoethyl)-3-bromobenzylamine (Example 8) | 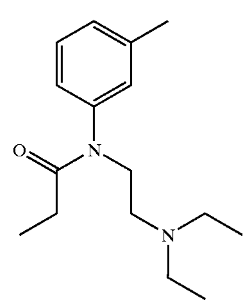 | 4.81 | N/A | N/A |

TABLE 1-continued

| Compound | Structure | IC$_{50}$ ($\mu$M) at $\alpha_2\delta$ binding site | Carrageenin induced thermal hyperalgesia in the rat | |
|---|---|---|---|---|
| | | | % MPE* 1 h post dose @ 30 mg/kg p.o. | % MPE* 2 h post dose @ 30 mg/kg p.o. |
| N-Propionyl, N-(2-Piperidylethyl)-1-amino-4-chloronaphthalene (Example 9) | 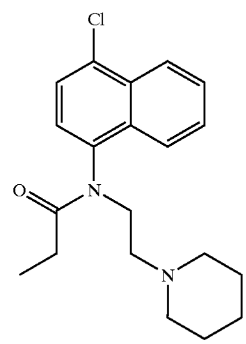 | >10 | N/A | N/A |
| N-Propionyl, N-(2-(3-dimethylaminopropyl))-1-amino-4-chloronaphthalene (Example 10) | 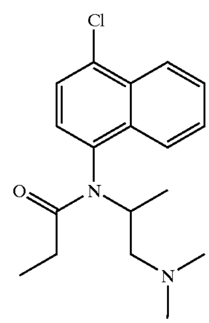 | 2.336 | N/A | N/A |
| N-Propionyl, N-(2-Dimethylaminoethyl)-1-amino-4-chloronaphthalene (Example 11) | 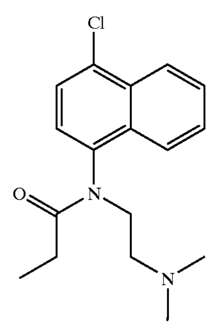 | 5.34 | N/A | N/A |
| N-Propionyl, N-(2-(N-benzyl)-aminoethyl)-1-aminonaphthalene (Example 12) | 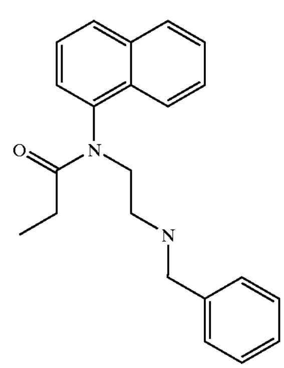 | >10 | 29.68 | 3.13 |

TABLE 1-continued

| Compound | Structure | IC$_{50}$ ($\mu$M) at $\alpha_2\delta$ binding site | Carrageenin induced thermal hyperalgesia in the rat | |
|---|---|---|---|---|
| | | | % MPE* 1 h post dose @ 30 mg/kg p.o. | % MPE* 2 h post dose @ 30 mg/kg p.o. |
| N-(2-Diethylaminoethyl)-N-(7-methyl-quinolin-4-yl)-propionamide (Example 13) | 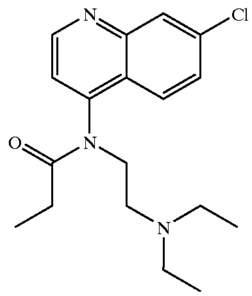 | 5.47 | 8.6 | 1.2 |
| N-Acryloyl, N-(2-Diethylaminoethyl)-1-amino-4-chloronaphthalene (Example 14) | 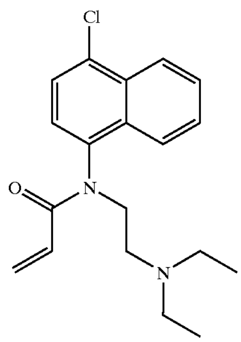 | 0.177 | 15.1 | 0.9 |
| N-Propionyl, N-(2-Diethylaminoethyl)-(1-amino-4-nitronaphthalene (Example 15) | 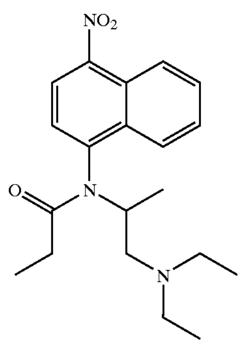 | 0.800 | −5.7 | 2.0 |

*MPE: maximum possible effect - set as baseline value prior to treatment with carrageenin As noted above, the invention compounds of Formula I are typically utilized in the form of pharmaceutical compositions for human therapy of CNS disorders. The compounds can be formulated with any excipient, diluent or carrier commonly utilized in the pharmaceutical art. Such common excipients include potato starch, corn starch, talc, sucrose, lactose, cellulose; flavoring agents such as peppermint, orange flavor and the like. Binders and lubricants such as magnesium stearate, colloidal silicon dioxide and gum tragacanth can be utilized for convenient oral or parenteral administration, for example as tablets, capsules, aqueous solutions, elixirs, syrups, and controlled release patches, pellets and suppositories, as well as solutions for IV, SC and IM injections. The formulations will typically contain from about 5% to about 95% of active compound of Formula I (w/w).

The preparations will be administered such that the active ingredient is presented at a dose which is effective to treat a CNS disorder. Such dose will generally be from about 0.1 to about 2000 mg/kg of body weight, typically about 1 mg to about 100 mg/kg. The formulations can be administered from 1 to about 4 times a day, or as otherwise dictated by the particular patient and condition being treated, and the attending medical practitioner.

The compounds of Formula I can additionally be utilized in combination with other active ingredients, for example selective serotonin re-uptake inhibitors such as fluoxetine hydrochloride, and any of the tricyclic antidepressants such as benzazepines and the like.

The following examples further illustrate specific formulations provided by this invention.

EXAMPLE 16

| Tablets | |
| --- | --- |
| N-Butyryl,N-(3-dimethylamino-propyl)-5-amino-indole | 200 mg |
| Potato starch | 50 mg |
| Magnesium stearate | 25 mg |
| Talc | 25 mg |

The above ingredients are blended to uniformity and then pressed into a tablet. Such tablets are administered from 1 to 4 times a day to an adult human suffering from depression and in need of treatment.

EXAMPLE 17

| Capsules | |
| --- | --- |
| N-pivaloyl 1-amino-2-trifluoromethyl-naphthalene | 300 mg |
| Corn starch | 50 mg |
| Dextrose | 50 mg |
| Magnesium oxide | 1 mg |

The above ingredients are blended to uniformity and filled into an empty telescoping gelatin capsule. Such capsules are administrated from 1 to 4 times a day to an adult human suffering from schizophrenia and in need of treatment.

EXAMPLE 18

| Parenteral solution | |
| --- | --- |
| N-propionyl,N-(2-diethylaminoethyl)(1-amino-4-bromonaphthalene), hydrochloride salt | 500 mg |
| isotonic saline | qs 1000 ml |

The invention compound is dissolved in 1000 ml of isotonic saline and filled into a sterile plastic bottle equipped with a drip tube. The solution is administered IV to a human suffering from chronic pain resulting from colon carcinoma.

EXAMPLE 19

| Transdermal skin patch | |
| --- | --- |
| N-acetyl, N-(3-(N-ethyl-N-isobutyl)aminopropyl-3-amino-6-bromofluorene | 450 mg |
| propylene glycol | 10 mg |
| elastomer | 5 mg |
| methyl cellulose | 50 mg |
| sodium carboxymethyl cellulose | 25 mg |

The above ingredients are blended and spread onto an elastic tape. The tape is applied to the skin surface of a mammal to prevent and treat migraine pain.

The compounds of Formula I are useful for treating all conditions resulting from disorders within the central nervous system in animals, including humans. Commonly treated conditions include pain, depression, anxiety and schizophrenia. Other conditions that can be treated according to this invention include seizure disorders, i.e. epilepsy, Huntington's disease, Parkinson's disease, amyotrophic lateral sclerosis (ALS), Alzheimer's disease, migraine, cerebral ischemia, and compulsive disorders such as narcotic addiction, alcoholism, smoking addiction, appetite disorders such as bulimia and obesity, sexual performance, and sleeping disorders.

What is claimed is:

1. A compound of formula I

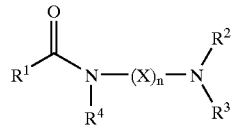

wherein $R^1$ is hydrogen, $C_1$–$C_4$ alkyl, or $C_2$–$C_4$ alkenyl;

$R^2$ and $R^3$ independently are hydrogen, $C_1$–$C_4$ alkyl, phenyl or benzyl;

X is $(CH_2)_n$, $CHMe$-$(CH_2)_{n-1}$ or $(CH_2)_{n-1}$—$CHMe$, n is 1, 2 or 3;

$R^4$ is an aromatic or heteroaromatic group selected from

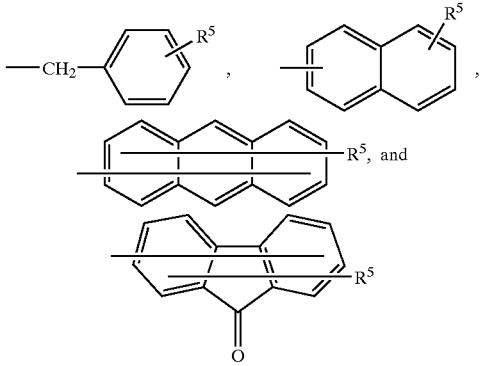

wherein $R^5$ is hydrogen, halogen, $C_1$–$C_4$ alkyl, nitro, $N_3$ or $CF_3$ and $R^6$ is hydrogen, $C_{1-4}$ alkyl, —

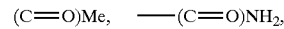

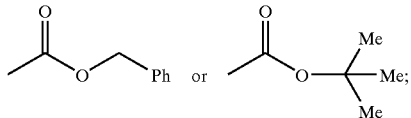

and the pharmaceutically acceptable salts thereof, with the proviso that in formula I:

when $R^1$ is H, $(X)_n$ is $(CH_2)_2$ and $R^2$ and $R^3$ are both ethyl, $R^4$ is not benzyl, 4-methylbenzyl, 4-chlorobenzyl, 2-chlorobenzyl, 4-bromobenzyl, 3-ethylbenzyl, 4 isopropylbenzyl, 4-n-propylbenzyl, 3-n-butylbenzyl, 2-t-butylbenzyl, 4-s-butylbenzyl or 2-bromobenzyl;

when $R^1$ is H, $(X)_n$ is $CH_r$ and $R^4$ is benzyl, $NR^2R^3$ is not $NHCH_2Ph$, NH-t-butyl, $N(CH_3)_2$ or $N(CH_2CH_3)_2$; and when $R^1$ is n-butyl, $(X)_n$ is $(CH_2)_2$ and $R^4$ is benzyl, $NR^2R^3$ is not $NHCH_2Ph$.

2. A compound according to claim 1 wherein R is $C_1$–$C_4$ alkyl.

3. A compound according to claim 2 wherein $R^1$ and $R^3$ independently are $C_1$–$C_4$ alkyl.

4. A compound according to claim 3 wherein n is 2 or 3.

5. A compound according to claim 4 wherein $R^4$ is selected from

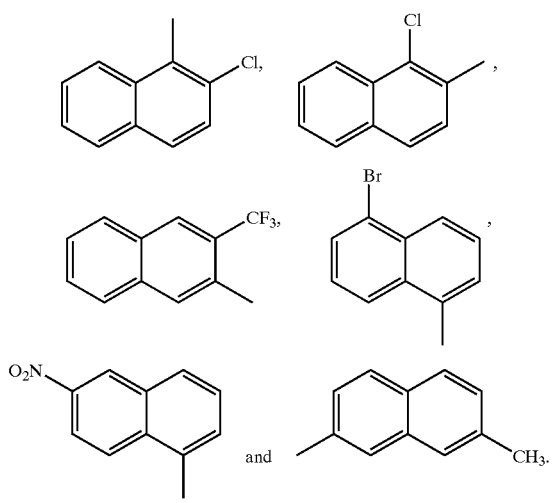

6. A compound according to claim 4 wherein $R^4$ is selected from

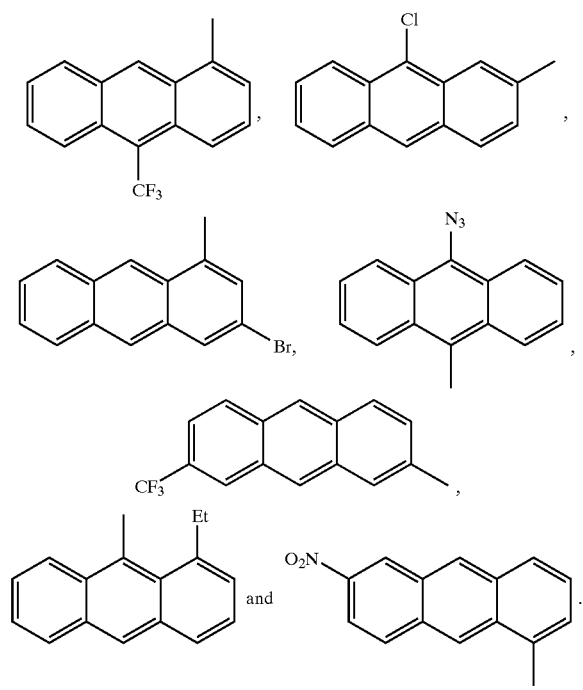

7. A compound according to claim 4 wherein $R^4$ is selected from

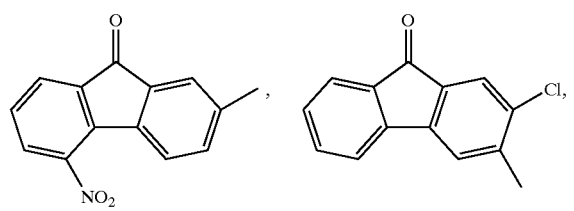

8. A compound according to claim 4 wherein $R^4$ is selected from

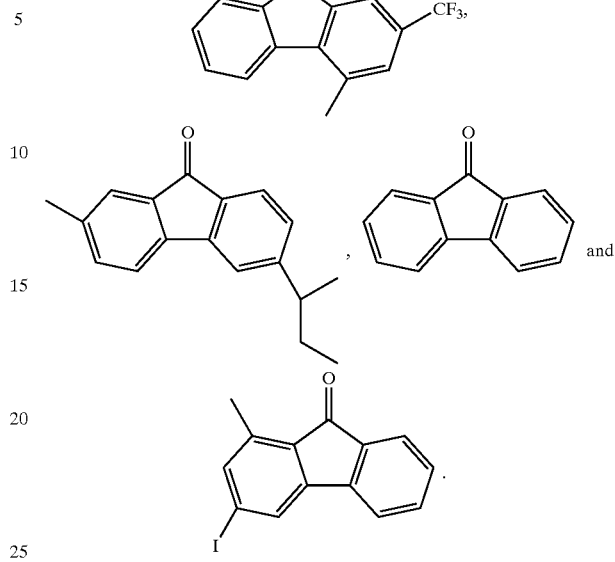

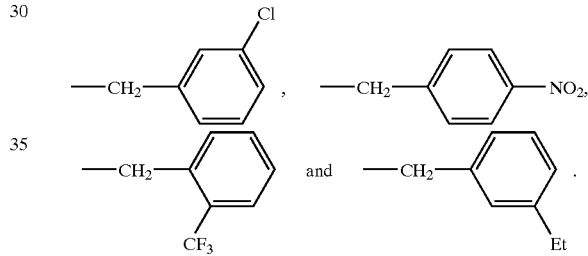

9. N-Propionyl, N-(2-Diethylaminoethyl)-1-amino-4-chloronaphthalene.

10. N-Propionyl, N-(2-Diethylaminoethyl)-4-amino-9-fluorenone.

11. N-Propionyl, N-(2-Diethylaminoethyl)-1-amino-4-bromonaphthalene.

12. N-Propionyl, N-3-diethylamino-2-propyl)-1-amino-4-chloronaphthalene.

13. N-Propionyl, N-(2-Diethylaminoethyl)-1-amino azidonaphthalene.

14. N-Acryloyl, N-(2-diethylaminoethyl)-1-amino-4-chloronaphtnalene.

15. N-Propionyl, N-(2-Diethylaminoethyl)-(1-amino-4-nitronaphthalene).

16. A compound according to claim 5 which is selected from
    N-Propionyl, N-(2-Diethylaminoethyl)-1-amino-4-chloronaphthalene;
    N-Propionyl, N-(2-Diethylaminoethyl)-4-amino-9-fluorenone;
    N-Propionyl, N-(2-Diethylaminoethyl)-1-amino-4-bromonaphthalene;
    N-Propionyl, N-(3-diethylamino-2-propyl)-1-amino-4-chloronaphthalene;
    N-Propionyl, N-(2-Diethylaminoethyl)-1-4-azidonaphthalene;

N-Propionyl, N-(2-Diethylaminoethyl)-3-chlorobenzyl-amine;

N-Propionyl, N-(2-Diethylaminoethyl)-3-bromobenzyl-amine;

N-Propionyl, N-(2-(3-Diethylamino-propyl)-1-amino-4-chloronaphthalene;

N-Propionyl, N-(2 Dimethylaminoethyl)-1-amino-4-chloronaphthalene;

N-Propionyl, N-(2-(N-benzyl)-aminoethyl)-1-aminonaphthalene;

N-Acryloyl, N-(2-diethylaminoethyl)-1-amino-4-chloronaphthalene; and

N-Propionyl, N-(2-Diethylaminoethyl)-(1-amino-4-nitronaphthalene).

17. A compound according to claim 1 which is a pharmaceutically acceptable salt.

18. A pharmaceutical formulation comprising a compound of claim 1 together with a pharmaceutically acceptable diluent, carrier or excipient therefor.

19. A method for treating a CNS disorder in a mammal in need of treatment comprising administering a CNS effective amount of a compound of claim 1.

20. A method for treating a CNS disorder in a mammal in need of treatment comprising administering a CNS effective amount of a compound

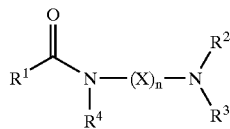

wherein:

$R^1$ is hydrogen, $C_{1-4}$ alkyl, or $C_2$–$C_4$ alkenyl;

$R^2$ and $R^3$ independently are hydrogen, $C_1$–$C_4$ alkyl, phenyl or benzyl;

X is $(CH_2)_{n-1}$, $CHMe$-$(CH_2)_{n-1}$ or $(CH_2)_{n-1}$—$CHMe$, n is 1, 2 or 3;

$R^4$ is am aromatic or heteroaromatic group selected from

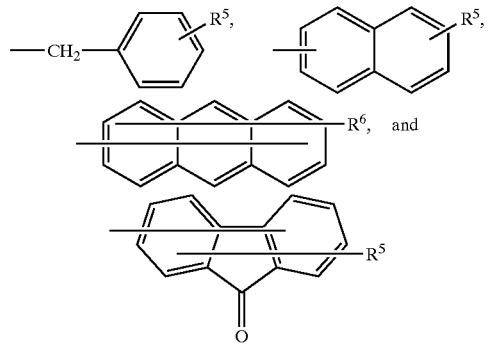

wherein $R^5$ is hydrogen, halogen, $C_1$–$C_4$ alkyl, nitro, $N_3$ or $CF_3$ and $R^6$ is hydrogen, $C_{1-4}$ alkyl, —

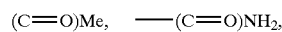

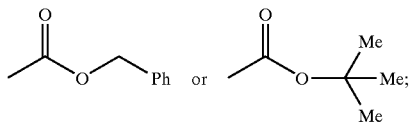

and the pharmaceutically acceptable salts thereof.

21. A method according to claim 19 wherein the CNS disorder is selected from pain, depression, anxiety, or schizophrenia.

22. A method according to claim 19 wherein the CNS disorder is selected from Huntington's disease, Alzheimer's disease or amyotrophic lateral sclerosis.

* * * * *